(12) United States Patent
Grot et al.

(10) Patent No.: US 7,155,077 B1
(45) Date of Patent: Dec. 26, 2006

(54) OPTICAL FIBER BASED SURFACE SENSING SYSTEM THAT ENABLES SPECTRAL MULTIPLEXING

(75) Inventors: Annette C. Grot, Cupertino, CA (US); Kai Cheung Chow, San Jose, CA (US)

(73) Assignee: Agilent Technologies, Inc, Santa Clara, CA (US)

( * ) Notice: Subject to any disclaimer, the term of this patent is extended or adjusted under 35 U.S.C. 154(b) by 0 days.

(21) Appl. No.: 11/158,529

(22) Filed: Jun. 21, 2005

(51) Int. Cl.
*G02B 6/00* (2006.01)
*G01J 1/04* (2006.01)
*H04J 14/02* (2006.01)

(52) U.S. Cl. .............................. 385/12; 385/88; 385/38; 250/227.11; 250/227.14; 250/227.18; 398/79; 398/82

(58) Field of Classification Search ................... 385/12, 385/13, 31, 39, 38, 88, 89, 92; 250/227.11, 250/227.14, 227.18, 227.19; 398/79, 82
See application file for complete search history.

(56) References Cited

U.S. PATENT DOCUMENTS

| | | | | |
|---|---|---|---|---|
| 4,717,240 A | * | 1/1988 | Gilby | ........................... 385/48 |
| 4,733,561 A | * | 3/1988 | Gilby | ........................... 73/579 |
| 5,513,913 A | * | 5/1996 | Ball et al. | ................... 374/120 |
| 5,708,735 A | * | 1/1998 | Benson et al. | ................. 385/12 |
| 6,590,647 B1 | * | 7/2003 | Stephenson | .................. 356/301 |
| 2004/0151626 A1 | | 8/2004 | Cunningham et al. | ... 422/82.11 |
| 2004/0175843 A1 | | 9/2004 | Roitman et al. | ............ 436/531 |

OTHER PUBLICATIONS

J. Homola, "Present and future of surface plasmon resonance biosensors", Anal. Bioanal Chem, vol. 377, p. 528, 2003.
A.G. Brolo, R. Gordon, B. Leathem, and K.L. Davanagh, "Surface Plasmon Sensor based on the enhanced light transmission through arrays of nanoholes in gold films", Langmuir, vol. 20, p. 4815, 2004.
R. Gordon, A.G. Brolo, A. McKinnon, A. Rajora, B. Leathem, and K.L. Kavanaugh, "Strong Polarization in the Optical Transmission through Elliptical Nanohole Arrays", Phys. Rev. Lett. vol. 92, p. 037401, 2004.
Joseph R. Lakowicz, "Radiative decay engineering 5: metal enhanced fluorescence and plasmon emission", Analytical Biochemistry, vol. 337 (2005), p. 171-194.

* cited by examiner

*Primary Examiner*—Brian M. Healy

(57) ABSTRACT

A surface sensing system including at least two sensors located on the end of the same optical fiber. The sensors are configured such that they exhibit resonant frequencies or Q-factors that are distinguishable from each other, where the Q-factor is defined as the resonant frequency divided by the resonance spectrum at full-width half maximum (FWHM). Because the sensors have distinguishable resonant frequencies or Q-factors and are located on the end of the same optical fiber, they can be monitored in parallel with little or no optical interference.

20 Claims, 9 Drawing Sheets

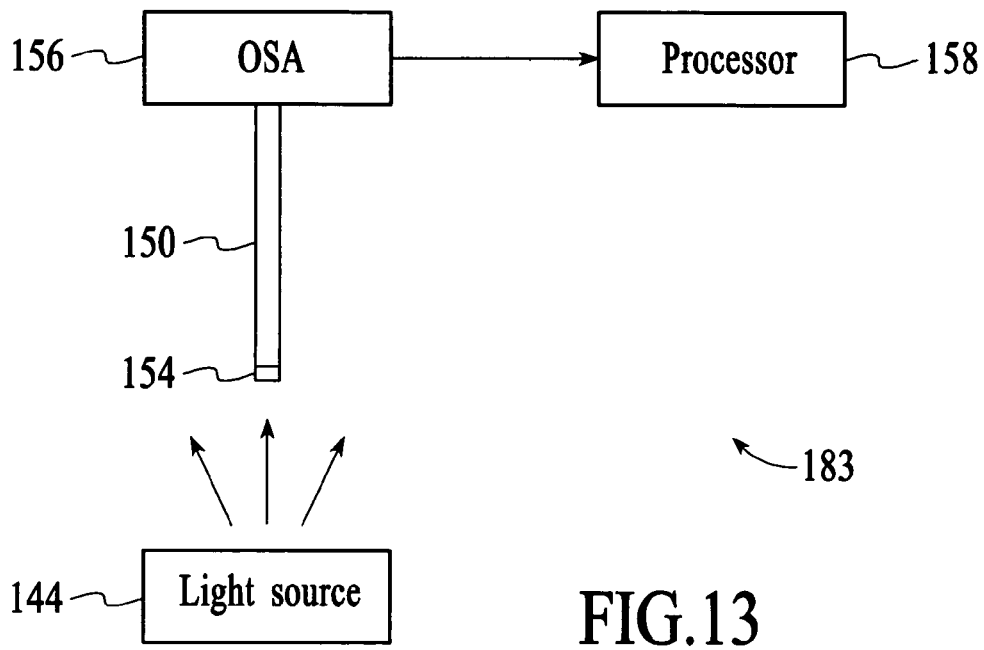

FIG.13

Expose first and second sensors to a test medium, wherein the first and second sensors are located on the end of the same optical fiber and confugured such that the first and second exibit resonant frequencies of Q-factors that are distinguishable from each other

⎯300

Inject an optical signal into the optical fiber such that the optical signal interacts with the first and second sensors in parallel

⎯302

Detect the optical signal after it has interacted with the first and second sensors

OPTICAL FIBER BASED SURFACE SENSING SYSTEM THAT ENABLES SPECTRAL MULTIPLEXING

BACKGROUND OF THE INVENTION

Surface sensing utilizes a surface condition or a change in a surface condition to measure a physical property of a test medium. In one surface sensing application, changes in the refractive index at the surface of a sensor can be measured. In another surface sensing application, surface conditions which increase the directionality of fluorescence can be used to detect a fluorescent material.

A surface sensor has been fabricated on the end of an optical fiber to create a single surface sensor that can be used, for example, to perform in-situ sensing. Although a single surface sensor located on the end of an optical fiber enables in-situ sensing, the throughput of the single surface sensor is limited to one test per fiber. The throughput of surface sensing systems is often a critical factor in achieving commercially viable sensing products.

SUMMARY OF THE INVENTION

In accordance with the invention, a surface sensing system includes at least two sensors located on the end of the same optical fiber. The sensors are configured such that they exhibit resonant frequencies or Q-factors that are distinguishable from each other, where the Q-factor is defined as the resonant frequency divided by the resonance spectrum at full-width half maximum (FWHM). The distinguishable resonant frequencies or Q-factors of the sensors can be achieved, for example, by fabricating the sensors with different spatial profiles of regions of high and low dielectric constant. Because the sensors have distinguishable resonant frequencies or Q-factors and are located on the end of the same optical fiber, they can be monitored in parallel with little or no optical interference. Monitoring multiple sensors, which have distinguishable resonant frequencies or Q-factors, in parallel is referred to herein as "spectral multiplexing." The sensors at the end of the same optical fiber can be monitored in parallel by injecting a swept optical signal into the optical fiber, where the wavelength range of the swept optical signal includes the resonant frequencies of both sensors, and detecting the swept optical signal with a single detector after the swept optical signal has interacted with the sensors. A surface sensor system that enables spectral multiplexing can be used, for example, in biosensing applications.

Other aspects and advantages of the present invention will become apparent from the following detailed description, taken in conjunction with the accompanying drawings, illustrated by way of example of the principles of the invention.

BRIEF DESCRIPTION OF THE DRAWINGS

FIG. 13 is another example of a spectral multiplexing system for use with a transmissive-type biosensor that is located on the end of an optical fiber.

FIG. 14 depicts a process flow diagram of a method for characterizing the binding of biological molecules in accordance with the invention.

Throughout the description similar reference numbers may be used to identify similar elements.

DETAILED DESCRIPTION

Figure 1A:
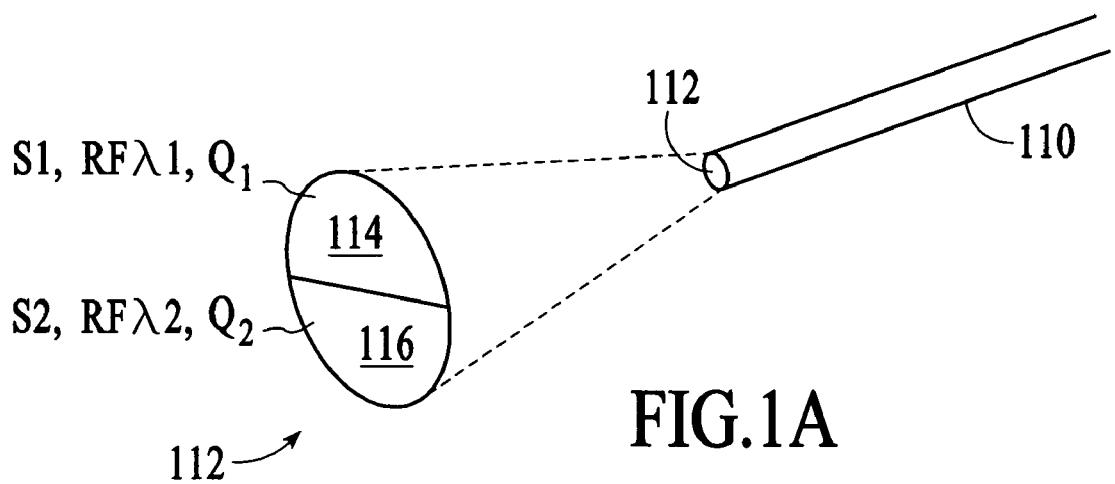
FIGS. 1A–1C depict an exemplary embodiment in accordance with the invention of two sensors with different resonant frequencies and/or Q-factors that are located on the end of the same optical fiber.
Figure 1B:
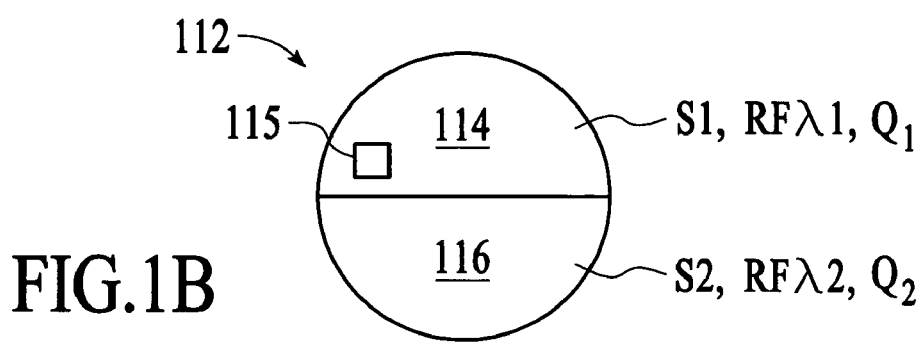
Figure 1C:
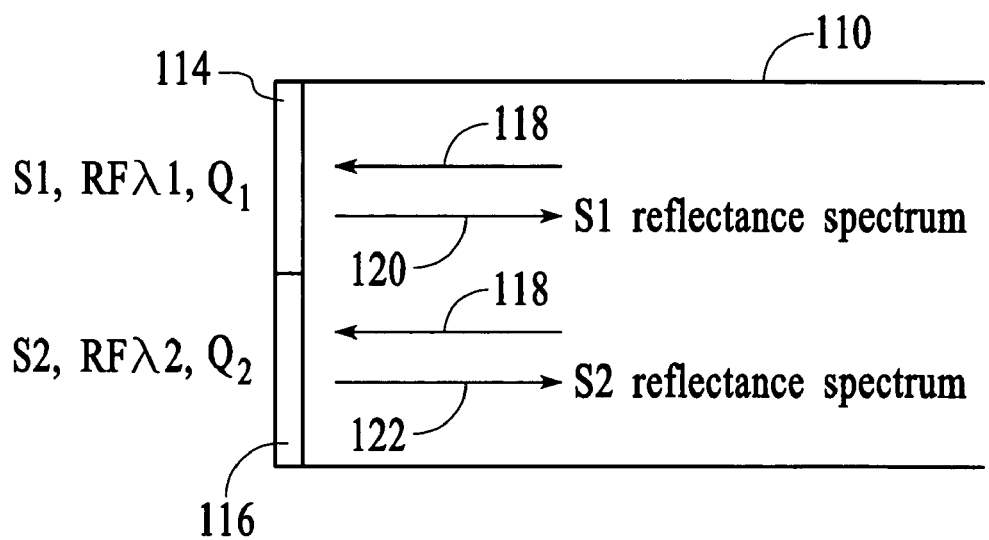

FIGS. 1A–1C depict an exemplary embodiment in accordance with the invention of two sensors with different resonant frequencies or Q-factors that are located on the end of the same optical fiber. FIG. 1A depicts a perspective view of an optical fiber 110, with an expanded view of the end 112 of the fiber that shows two sensors, S1 114 and S2 116. In the example of FIG. 1A, the resonant frequency and Q-factor of sensor S1 114 are identified as $RF_{\lambda,1}$ and $Q_1$, respectively, and the resonant frequency and Q-factor of sensor S2 116 are identified as $RF_{\lambda,2}$ and $Q_2$, respectively. FIG. 1B depicts a straight on view of the fiber end 112 and the two sensors 114 and 116 from FIG. 1A. FIG. 1C depicts a side view of the fiber 110 and the two sensors 114 and 116 from FIGS. 1A and 1B.

Figure 2:
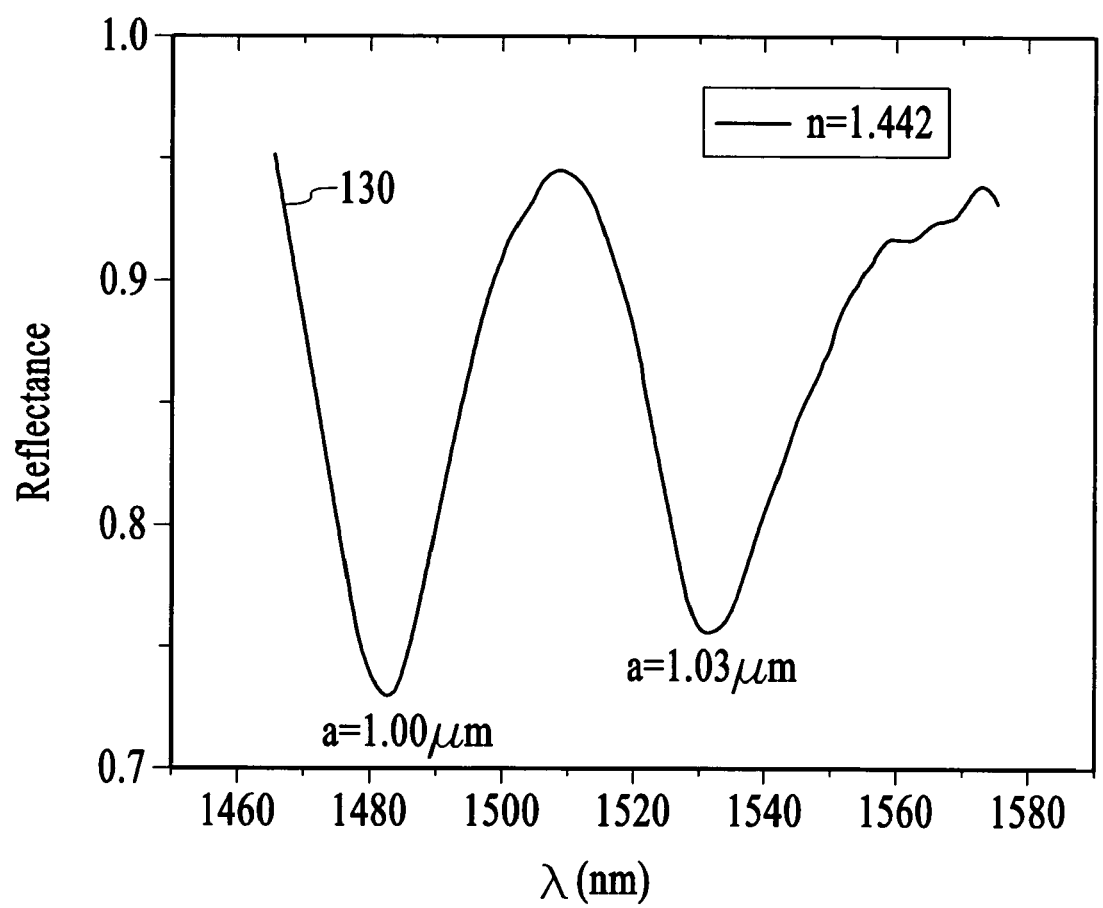
FIG. 2 is a graph of reflectance vs. wavelength for the two sensors of FIGS. 1A–1C.

In accordance with the invention, the two sensors depicted with reference to FIGS. 1A–1C are configured such that they exhibit resonant frequencies or Q-factors that are distinguishable from each other. Examples of types of sensors and techniques for configuring the sensors to exhibit the desired resonant frequencies and Q-factors are described below. For description purposes, it is assumed that the two sensors are configured such that their resonant frequencies are distinguishable from each other. FIG. 2 is a graph of reflectance vs. wavelength for the two sensors 114 and 116 of FIGS. 1A–1C for the case in which the two sensors have distinguishable resonant frequencies. As depicted in FIG. 2, the reflectance spectrums 130 of the two sensors are spectrally spaced such that the resonant frequencies of the two sensors can readily be distinguished from each other. The spectral spacing between the reflectance spectrums 130 of the two sensors can be narrower as long as the resonant frequencies can still be distinguished.

To characterize one or more physical properties of a test medium using the surface sensor system described with reference to FIGS. 1A–1C, the two sensors 114 and 116 are exposed to a test medium (not shown). For example, the test medium can be a liquid and the optical fiber end that includes the two sensors is placed into the liquid. Referring to FIG. 1C, an optical signal 118 is injected into the optical fiber such that the optical signal interacts with both of the sensors in parallel. Light that is reflected from the two sensors is measured and the measured reflectance spectrums are used to determine the resonant frequencies and/or reflectance spectrums of the sensors. In an embodiment, the optical signal is injected into the optical fiber before the two sensors are exposed to the test medium as well as while the two sensors are exposed to the test medium so that changes in the resonant frequencies can be measured. Changes in the resonant frequencies are used to characterize one or more physical properties of the test medium. Because the two sensors have distinguishable resonant frequencies, multiple characterizations can be carried out in parallel. For example, in a biosensing application, the affinity between two different sets of biomolecules can be measured in parallel.

In order for two characterizations to be carried out in parallel, the sensors depicted in FIGS. 1A–1C must exhibit either distinguishable resonant frequencies or distinguishable Q-factors. The two sensors could exhibit both distinguishable resonant frequencies and distinguishable Q-factors although this is not required.

Figure 3A:
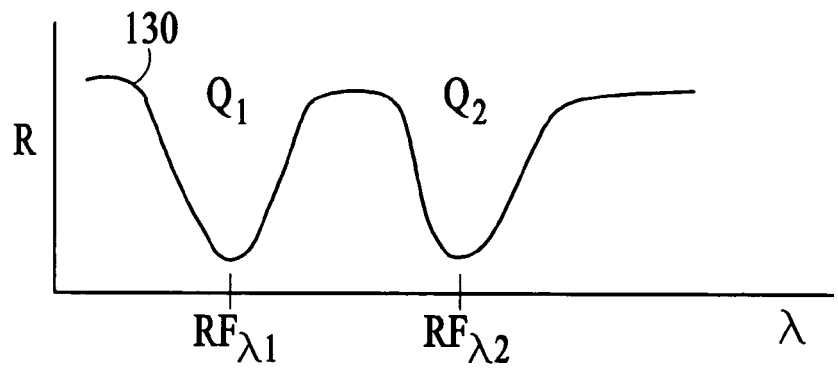
FIGS. 3A and 3B depict the reflectance spectrums of two sensors that are measured in parallel for the case in which the two sensors exhibit distinguishable resonant frequencies (e.g., $RF_{\lambda,1} \neq RF_{\lambda,2}$) and indistinguishable Q-factors (i.e., $Q_1 = Q_2$).
Figure 3B:
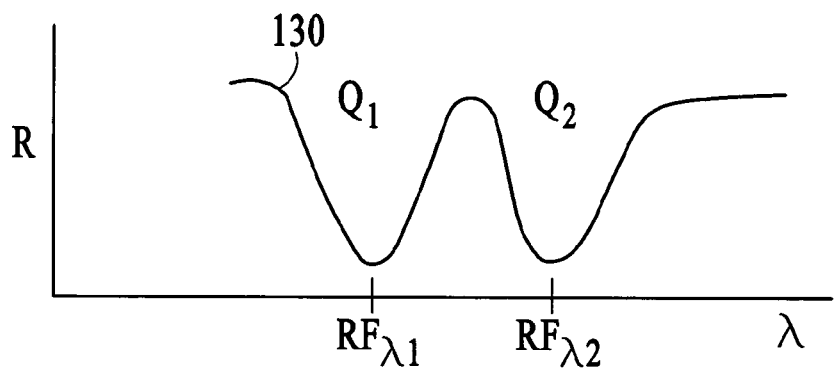

FIG. 3A depicts the reflectance spectrums 130 of two sensors that are measured in parallel for the case in which the two sensors exhibit distinguishable resonant frequencies (e.g., $RF_{\lambda,1} \neq RF_{\lambda,2}$) and indistinguishable Q-factors (i.e., $Q_1 = Q_2$). As the reflectance spectrums of the two sensors change in response to exposure to a test medium, the resonant frequencies remain distinguishable from each other. FIG. 3B depicts the reflectance spectrums of the two sensors after the resonant frequencies have shifted. Although the resonant frequencies have shifted, they remain distinguishable from each other over the entire spectral bandwidth of the optical signal.

Figure 4A:
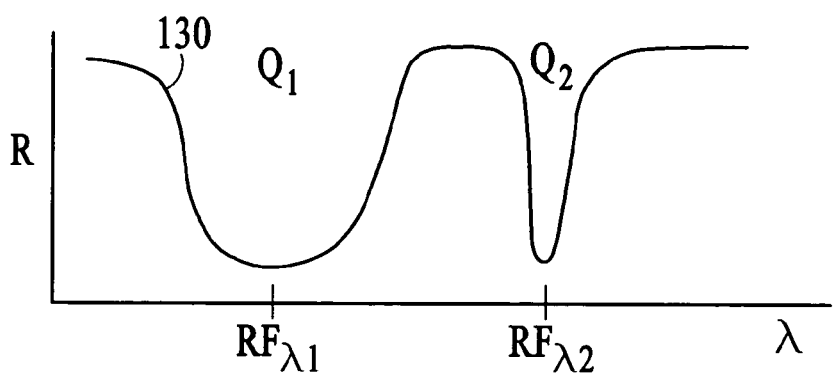
FIGS. 4A and 4B depict the reflectance spectrums of two sensors that are measured in parallel for the case in which the two sensors exhibit distinguishable Q-factors (e.g., $Q_1 \neq Q_2$).
Figure 4B:
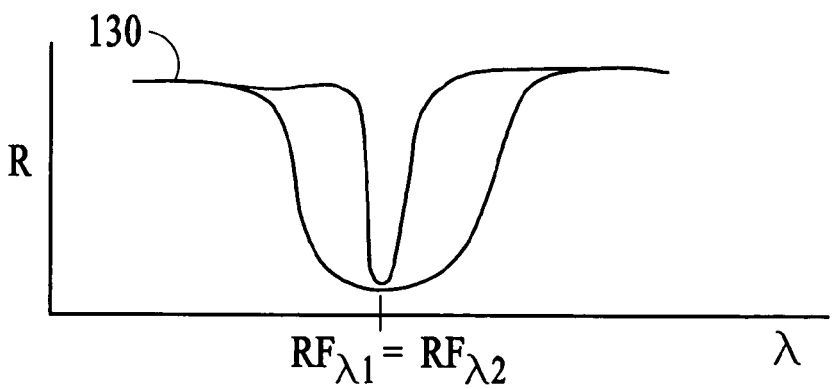

FIG. 4A depicts the reflectance spectrums 130 of two sensors that are measured in parallel for the case in which the two sensors exhibit distinguishable Q-factors (e.g., $Q_1 \neq Q_2$). Although the Q-factors exhibited by the two sensors are distinguishable, the resonant frequencies of the two sensors may not be distinguishable under all test conditions. FIG. 4B depicts the case in which the reflectance spectrums of the two sensors have shifted such that the resonant frequencies of the two sensors are indistinguishable from each other. Although the resonant frequencies of the two sensors are indistinguishable from each other (e.g., $RF_{\lambda,1} = RF_{\lambda,2}$), the reflectance spectrums of the two sensors can still be distinguished from each other because of the different Q-factors. The resonant frequencies and Q-factors exhibited by the sensors are considered to be distinguishable from each other when the optical responses of the sensors can be individually recognized using, for example, high resolution optical detection systems and techniques.

Figure 5A:
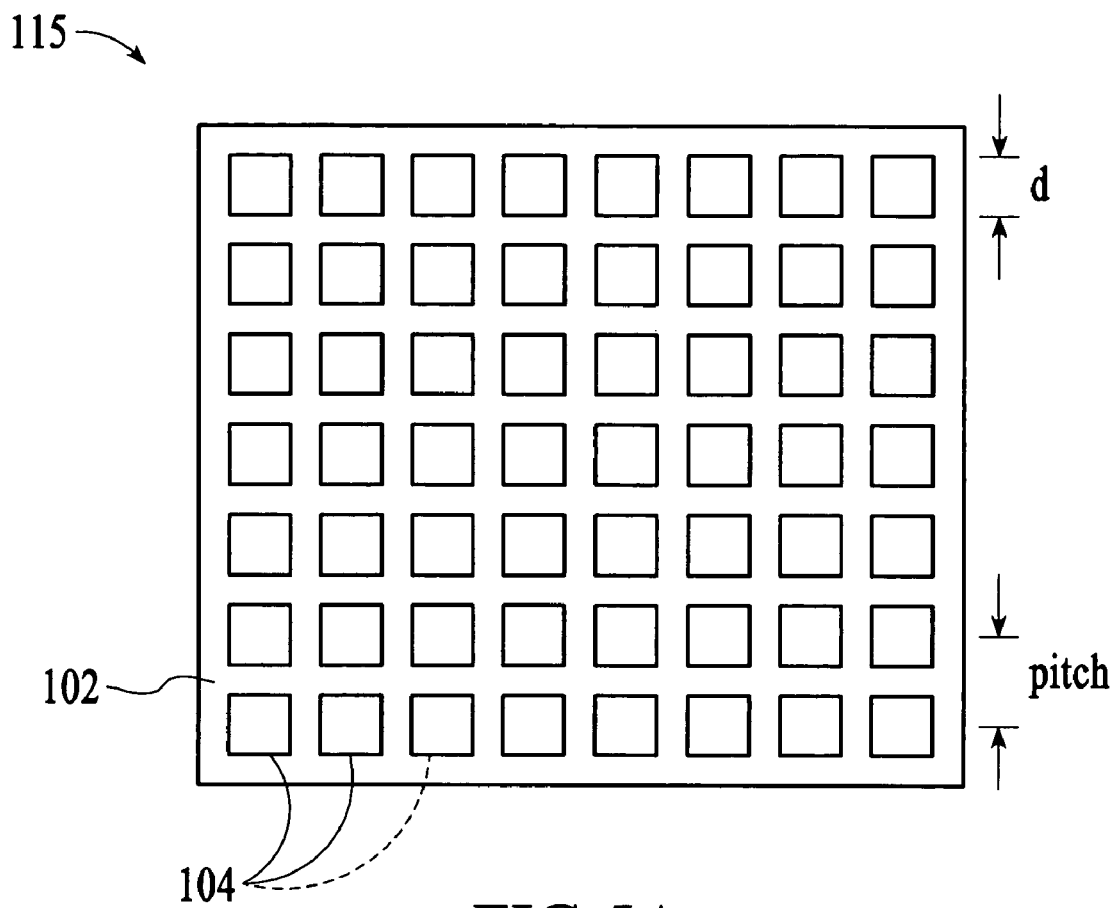
FIG. 5A depicts an expanded view of a section of a grating-based sensor that can be used in the system of FIGS. 1A–1C.
Figure 5B:
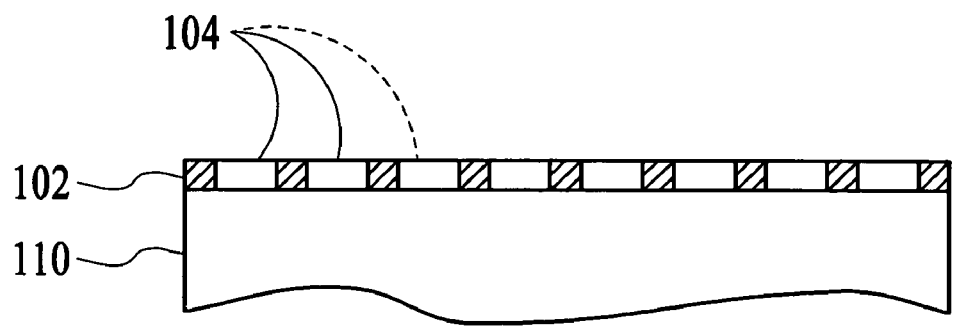
FIG. 5B is a side view of the grating-based sensor from FIG. 5A.

In one embodiment, the sensors are gratings which are fabricated on the end of an optical fiber. FIG. 5A depicts an expanded view of a section 115 of a grating-based sensor (e.g., section 15 of sensor 114 as depicted in FIG. 1B) that can be used in the system of FIGS. 1A–1C. The grating-based sensor has a spatial profile that includes regions of high and low dielectric constant 102 and 104, where the spatial profile is the two-dimensional profile of the sensor's top surface. The regions of low dielectric constant are referred to as low dielectric constant features 104 and the remaining portion of the sensor is the region of high dielectric constant 102. The low dielectric constant features 104 typically exhibit a repeating pattern with each feature being essentially the same size and shape. The sensor is fabricated on an end 112 of the optical fiber 110 by depositing, for example, a gold layer onto the surface of the optical fiber end to form the region of high dielectric constant 102. The regions of low dielectric constant 104 are typically square holes in the gold layer. FIG. 5B is a side view of the sensor section that shows the optical fiber 110 and the regions of high and low dielectric constant 102 and 104 located on the end of the optical fiber 110. The square holes depicted in FIGS. 5A and 5B are defined by a length dimension, d, and a pitch (also referred to as the lattice constant), a, where the pitch is the distance between the centers of adjacent features (e.g., the square holes). Grating-based sensors such as the one depicted in FIGS. 5A and 5B can be fabricated onto the end of an optical fiber using various techniques including known semiconductor processing techniques such as optical lithography, imprint lithography, lift-off, and etching. The grating-based sensors can be formed using other materials including, for example, Al, Ag, or non-conducting dielectrics such as $TiO_2$ or $Si_3N_4$.

Many aspects of each sensor's design affect the resonant frequency and Q-factor of the particular sensor. For example, the resonant frequency and Q-factor of a particular sensor can be affected by the optical fiber composition, the composition and thickness of the high dielectric constant region, the composition and thickness of the low dielectric constant features, the size and shape of the low dielectric constant features, the pattern symmetry (e.g., square or hexagon) of the low dielectric constant features, and the pitch of the low dielectric constant features. The resonant frequency and/or Q-factor of a sensor design can be changed by changing the spatial profile of the regions of high and low dielectric constant. For example, changing only one aspect of a sensor's spatial profile, such as the size or pitch of the low dielectric constant features, will change the resonant frequency and/or Q-factor of the sensor.

In the example of FIGS. 1A–1C, the resonant frequencies of the two sensors 114 and 116 can be made different by fabricating square holes (not shown) in a gold layer at different pitches as described with reference to FIGS. 5A and 5B. For example, the pitch of the square holes in the first sensor 114 is 1,000 nm (a=1.00 um) and the pitch of the square holes in the second sensor 116 is 1,030 nm (a=1.03 um). In another embodiment, the Q-factors of the two sensors 114 and 116 can be made different by fabricating the square holes in different sizes. For example, the square holes in the first sensor can have 200 nm sides while the square holes of the second sensor can have 500 nm sides. By varying the size of the square holes of the two sensors from 200 nm–500 nm (on a period of 1 um), it is possible to change the linewidth of the resonance of the two sensors from 3 nm–90 nm.

Figure 6A:
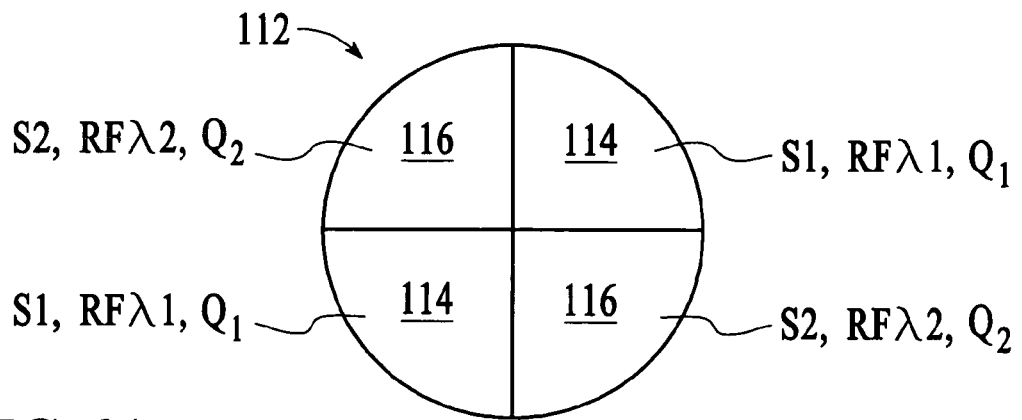
FIGS. 6A–6C show examples of alternative configurations of two sensors that are located on the end of the same optical fiber.
Figure 6B:
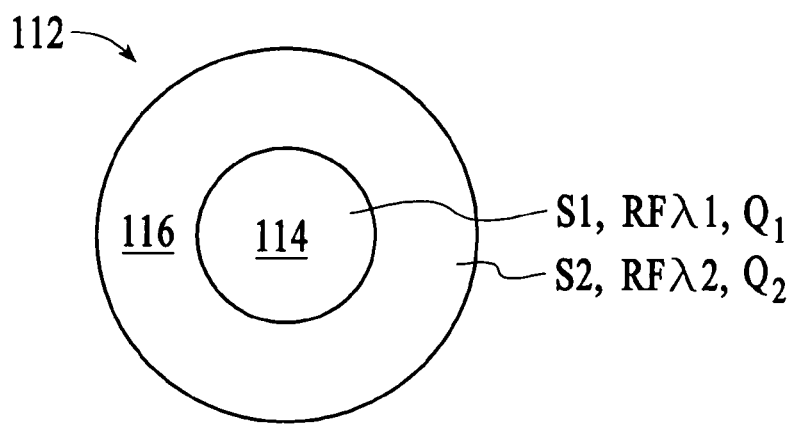
Figure 6C:
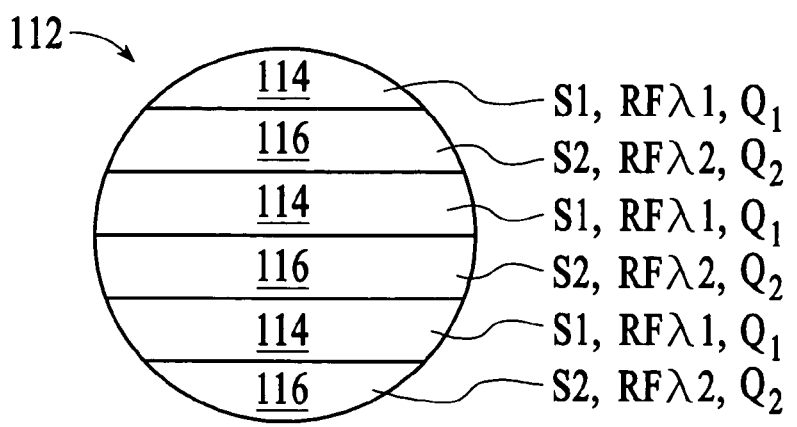

In the example of FIGS. 1A–1C, the two sensors 114 and 116 each cover non-overlapping halves of the surface area of the optical fiber end 112. Although the two sensors shown in FIGS. 1A–1C are divided down the center of the optical fiber end, other configurations of two sensors on the end of the optical fiber are possible. FIGS. 6A–6C show examples of alternative configurations of the two sensors 114 and 116 that are located on the end 112 of an optical fiber. FIG. 6A depicts an exemplary configuration in which the two sensors 114 and 116 cover alternating quadrants of the optical fiber end. In particular, sensor S1 has resonant frequency $RF_{\lambda,1}$ and Q-factor $Q_1$ and covers the upper right and lower left quadrants of the optical fiber end while sensor S2 has resonant frequency $RF_{\lambda,2}$ and Q-factor $Q_2$ and covers the lower right and upper left quadrants of the optical fiber end. FIG. 6B depicts an exemplary configuration in which the two sensors 114 and 116 cover concentric circular areas of the optical fiber end 112. In particular, sensor S1 covers an inner circle area of the optical fiber end and sensor S2 covers an outer ring area of the optical fiber end. FIG. 6C depicts an exemplary embodiment in which the two sensors 114 and 116 cover alternating horizontal slices of the optical fiber end 112. In the configurations of FIGS. 6A–6C, the surface areas of the two sensors are approximately equal, although other distribution ratios of the sensor surface areas are possible.

Figure 7A:
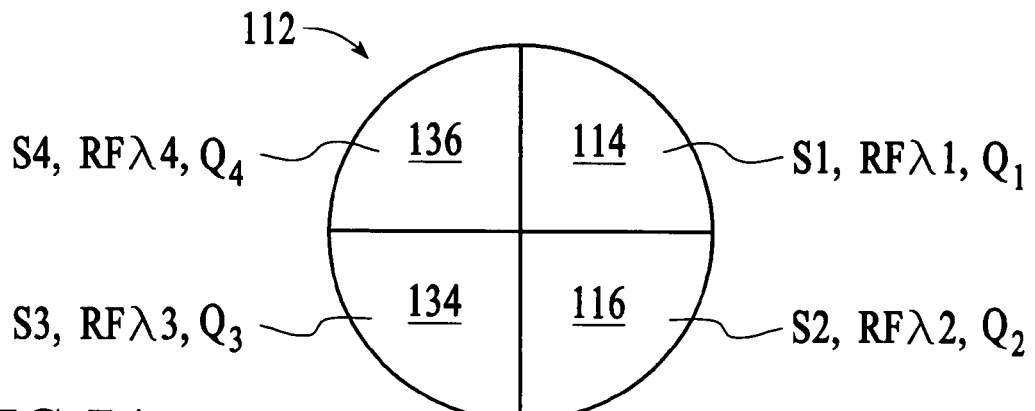
FIGS. 7A–7C depict exemplary configurations of biosensors that include four distinct sensors, each having a different resonant frequency, located on the end of the same optical fiber.
Figure 7B:
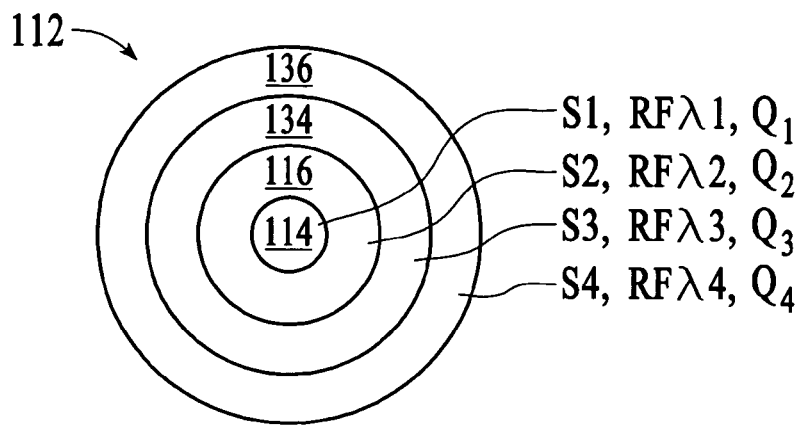
Figure 7C:
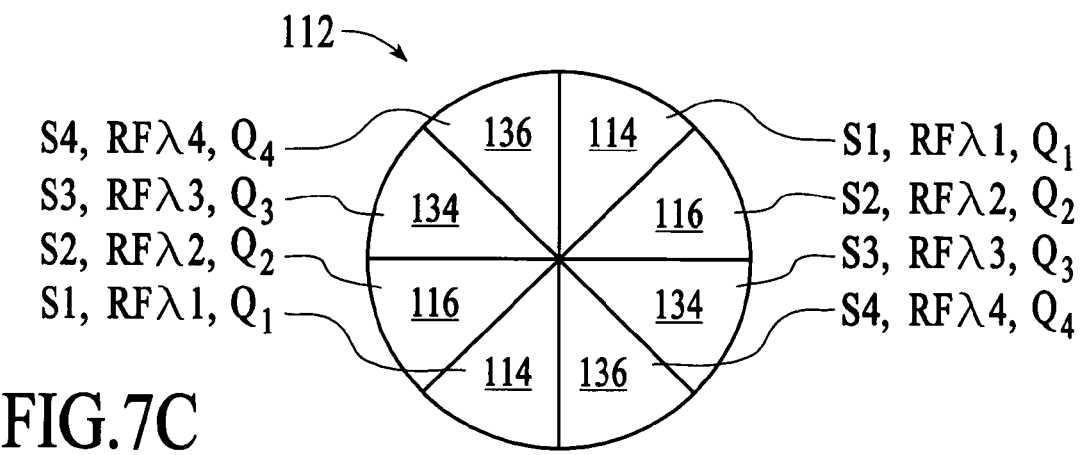

Although the surface sensing systems described above have only two sensors 114 and 116 with different resonant frequencies and/or Q-factors located on the end 112 of the same optical fiber 110, a surface sensing system with more than two sensors having different resonant frequencies and/or Q-factors can be located on the end of the same optical fiber. FIGS. 7A–7C depict exemplary configurations of surface sensing systems that include four distinct sensors 114, 116, 134, and 136, each having a different resonant frequency and/or Q-factor, located on the end 112 of the same optical fiber. With reference to FIG. 7A, the fiber end is divided into four quadrants, with a different sensor being located in each quadrant. Sensor S1 114 is in the upper right quadrant and has a resonant frequency $RF_{\lambda,1}$ and a Q-factor $Q_1$, sensor S2 116 is in the lower right quadrant and has a resonant frequency $RF_{\lambda,2}$ and a Q-factor $Q_2$, sensor S3 134 is in the lower left quadrant and has a resonant frequency $RF_{\lambda,3}$ and a Q-factor $Q_3$, and sensor S4 136 is in the upper left quadrant and has a resonant frequency $RF_{\lambda,4}$ and a Q-factor $Q_4$. With reference to FIG. 7B, the sensor is divided into concentric rings, with each different sensor being located in a different ring. As with the sensor of FIG. 5A, sensor S1 114 has a resonant frequency $RF_{\lambda,1}$ and a Q-factor $Q_1$, sensor S2 116 has a resonant frequency $RF_{\lambda,2}$ and a Q-factor $Q_2$, sensor S3 134 has a resonant frequency $RF_{\lambda,3}$ and a Q-factor $Q_3$, and sensor S4 136 has a resonant frequency $RF_{\lambda,4}$ and a Q-factor $Q_4$. With reference to FIG. 7C, the sensor is divided into $1/8^{th}$ pie slices and each of the four sensors includes two non-adjacent pie slices. Again, sensor S1 114 has a resonant frequency $RF_{\lambda,1}$ and a Q-factor $Q_1$, sensor S2 116 has a resonant frequency $RF_{\lambda,2}$ and a Q-factor $Q_2$, sensor S3 134 has a resonant frequency $RF_{\lambda,3}$ and a Q-factor $Q_3$, and sensor S4 136 has a resonant frequency $RF_{\lambda,4}$ and a Q-factor $Q_4$. The different resonant frequencies and/or Q-factors can be achieved, for example, by fabricating the sensors onto the optical fiber end with the low dielectric constant features of the two sensors being at different pitches and/or of different sizes.

Figure 8:
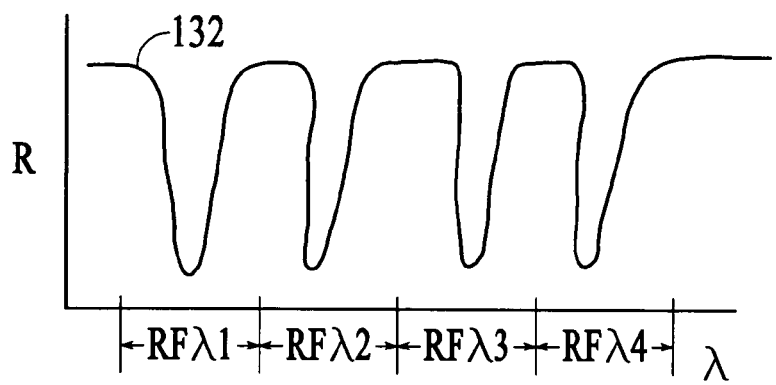
FIG. 8 is a graph of reflectance vs. wavelength for the four sensors of any of the biosensor configurations from FIGS. 5A–5C.

FIG. 8 is a graph of reflectance vs. wavelength for the four sensors 114, 116, 134, and 136 of any of the sensor configurations from FIGS. 7A–7C. The reflectance of the four sensors is measured in parallel by, for example, injecting a swept optical signal into the fiber. As depicted in FIG. 8, the reflectance spectrums 132 of the four sensors are spectrally spaced such that the resonant frequencies of the four sensors can readily be distinguished from each other using a single detector. The spectral spacing between the resonance spectrums 132 of the four sensors can be smaller as long as the resonant frequencies can still be distinguished. With smaller spectral spacing, more distinguishable channels can be included within the same spectral bandwidth. More distinguishable channels can also be included within the same spectral bandwidth by narrowing the spectral profiles of the sensors (i.e., increasing the Q-factors of the sensors).

In general, the surface sensing systems described above can be designed to work in reflection or transmission. If the surface sensing systems are designed to work in reflection, the resonant frequencies of the sensors are identified by dips or minimums in the reflectance spectrums. If the surface sensing systems are designed to work in transmission, the resonant frequencies are identified by peaks or maximums in the transmission spectrums.

To achieve spectral multiplexing using a surface sensing system as described above, there needs to be an optical signal, a way to apply the optical signal to the optical fiber end, and a way to detect the portions of the optical signal that are either reflected or transmitted to identify changes in the resonant frequencies of the sensors. The basic functions of a spectral multiplexing system that uses reflective-type sensors include; 1) providing an optical signal that includes the resonant frequencies of the sensors, 2) injecting the optical signal into the optical fiber that includes the sensors located on the end, 3) collecting the portions of the optical signal that are reflected from the sensors, and 4) detecting the reflected portion of the optical signal. There are many configurations of a spectral multiplexing system that can be used to provide the above-described functions and the exact configuration is not critical to the invention as long as the above-described functions are provided.

Figure 9:
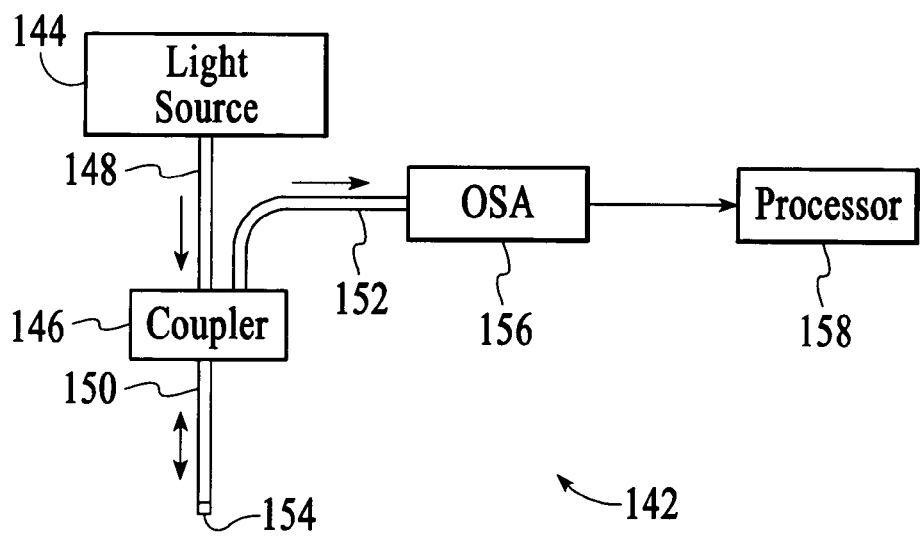
FIG. 9 is an example of a spectral multiplexing system for use with a reflective-type biosensor that is located on the end of an optical fiber.

One example of a spectral multiplexing system 142 for use with a reflective-type surface sensing system is depicted in FIG. 9. The spectral multiplexing system 142 of FIG. 9 includes a light source 144, a coupler 146, fibers 148, 150, and 152, a surface sensing system 154 with at least two sensors (not shown) with distinguishable resonant frequencies and/or Q-factors located on the end of optical fiber 150, an optical spectrum analyzer (OSA) 156, and a processor 158. In the example of FIG. 9, the light source provides an optical signal with a broadband energy spectrum that includes the resonant frequencies of the sensors on the end of the optical fiber. While the sensors are used to measure changes in refractive index, the sensor measurements can be applied to the measurement of biomolecules. In particular, biomolecules can be measured with specificity using multiple sensors on the end of the same optical fiber by immobilizing different capture agents on the sensors before exposing the sensors to a test medium. In an embodiment, capture agents are applied to the sensors located on the end of the optical fiber. Many different capture agents and techniques for applying capture agents to the sensors can be used. In a biosensing application, the capture agents may include one or more antibodies that are selected because of their affinity to certain proteins of interest. The capture agents can be applied as monolayers of less than 50 nm thick. Once the capture agents are applied to the sensors, the sensors and capture agents are exposed to the test medium, which may include proteins that have a high affinity to one or more of the antibodies of the capture agents. Techniques for exposing the sensors and capture agents to the test medium (including in-situ techniques) are known in the field and are not described further herein. Because the refractive index of the proteins in the test medium are different from the refractive index of the test medium as a whole, the refractive index at the sensor will change, thereby changing the resonant frequency of the particular sensor.

To monitor bindings at the sensors between the antibodies and proteins, a broadband optical signal from the light source 144 is injected into optical fiber 148. The optical signal propagates through optical fiber 148, coupler 146, and optical fiber 150 to the sensors that are located on the end of optical fiber 150. Because the sensors are located on the end of the same optical fiber, the optical signal interacts in parallel. The sensors absorb optical energy at their respective resonant frequencies and reflect a portion of the optical signal back towards the coupler 146. The coupler 146 couples the reflected optical signal into optical fiber 152 and optical fiber 152 directs the reflected optical signal to the OSA 156. The OSA 156 measures the intensity of the reflected optical signal as a function of wavelength and provides intensity vs. wavelength information to the processor 158. The intensity vs. wavelength information is used to identify shifts in the resonant frequencies of the sensors that result from bindings of molecules between the antibodies and proteins at the sensors. Shifts in the resonant frequencies of the sensors are used to characterize one or more physical properties of the test medium.

Figure 10:
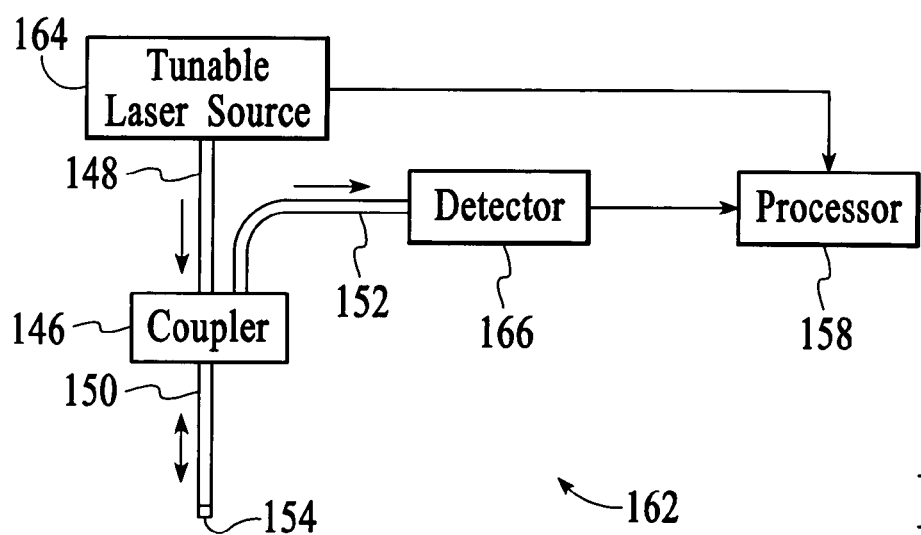
FIG. 10 is another example of a spectral multiplexing system for use with a reflective-type biosensor that is located on the end of an optical fiber.

Another example of a spectral multiplexing system 162 for use with a reflective-type surface sensing system is depicted in FIG. 10. The spectral multiplexing system 162 of FIG. 10 includes a tunable laser source 164, a coupler 146, optical fibers 148, 150, and 152, a surface sensing system 154 with at least two sensors (not shown) of different resonant frequency and/or Q-factor located on the end of optical fiber 150, a detector 166, and a processor 158. In the example of FIG. 10, the tunable laser source 164 generates an optical signal with a narrowband optical energy spectrum that can be swept across a range of wavelengths that includes the resonant frequencies of the sensors on the end of optical fiber 150. In an exemplary operation, capture agents are applied to the sensors as described above. Once the capture agents are applied to the sensors, the capture agents are exposed to the test medium as described above.

To monitor bindings at the sensors, the tunable laser source 164 generates an optical signal that is swept across a range of wavelengths, where the range of wavelengths includes the resonant frequencies of the sensors. The swept optical signal is injected into optical fiber 148 and propagates through the coupler 146 to the sensors at the end of optical fiber 150. Because the sensors are located on the end of the same optical fiber 150, the optical signal interacts in parallel. As the optical signal sweeps across a range of wavelengths, the sensors absorb optical energy that is at the resonant frequencies of the sensors. Portions of the swept optical signal that are not absorbed are reflected back up optical fiber 150 to the coupler 146. The coupler 146 couples the reflected optical signal to optical fiber 152 and the optical signal propagates to the detector 166. The detector 166 measures the optical intensity of the collected optical signal and delivers intensity information to the processor 158. The processor 158 receives wavelength information from the tunable laser source 164 and the intensity information from the detector 166 and uses the information to generate intensity vs. wavelength information. The intensity vs. wavelength information is used to identify shifts in the resonant frequencies of the sensors that result from bindings between the antibodies and proteins at the sensors. Shifts in the resonant frequencies of the sensors are used to characterize one or more physical properties of the test medium.

The basic functions of a spectral multiplexing system that uses transmissive-type sensors include; 1) providing an optical signal that includes the resonant frequencies of the sensors, 2) injecting the optical signal into the optical fiber that includes the sensors at the end, 3) collecting the portions of the optical signal that pass through the sensors, and 4) detecting the passed portions of the optical signal. There are many configurations of a spectral multiplexing system that can be used to provide the above-described functions and the exact configuration is not critical to the invention as long as the above-described functions are provided.

Figure 11:
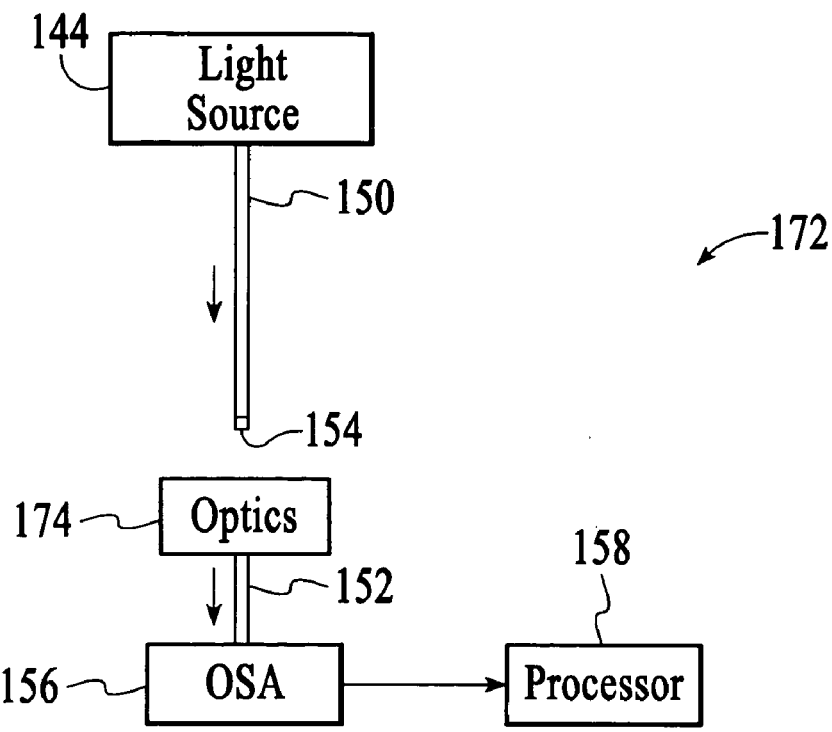
FIG. 11 is an example of a spectral multiplexing system for use with a transmissive-type biosensor that is located on the end of an optical fiber.

One example of a spectral multiplexing system 172 for use with a transmissive-type surface sensing system is depicted in FIG. 11. The spectral multiplexing system 172 of FIG. 11 includes a light source 144, optical fibers 150 and 152, a surface sensing system 154 with at least two sensors (not shown) of different resonant frequency and/or Q-factor located on the end of optical fiber 150, optics 174, an OSA 156, and a processor 158. The spectral multiplexing system 172 is similar to the spectral multiplexing system 142 described with reference to FIG. 9 except that the spectral multiplexing system 172 of FIG. 11 monitors light that passes through the sensors on the end of the optical fiber 150 instead of light that reflects off of the sensors. In operation, the optics 174 direct light that passes through the sensors to the OSA 156. The rest of the operation is essentially the same as described above with reference to FIG. 9.

Figure 12:
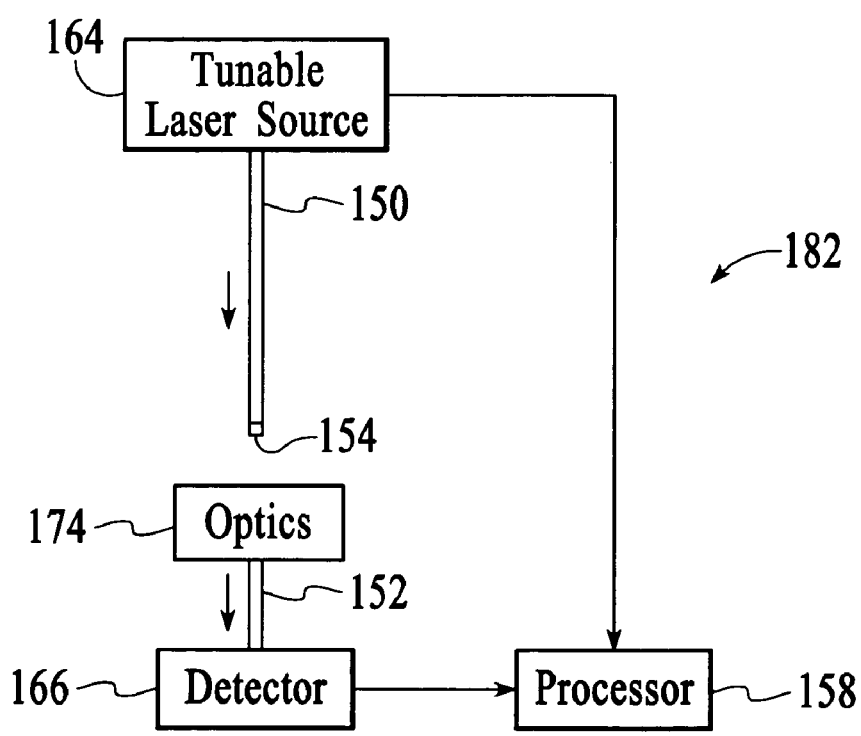
FIG. 12 is another example of a spectral multiplexing system for use with a transmissive-type biosensor that is located on the end of an optical fiber.

Another example of a spectral multiplexing system 182 for use with a transmissive-type sensor is depicted in FIG. 12. The spectral multiplexing system 182 of FIG. 12 includes a tunable laser source 164, fibers 150 and 152, a surface sensing system 154 with at least two sensors (not shown) of different resonant frequency and/or Q-factor located on the end of optical fiber 150, optics 174, a detector 166, and a processor 158. The spectral multiplexing system 182 is similar to the spectral multiplexing system 162 described with reference to FIG. 10 except that the spectral multiplexing system 182 of FIG. 12 monitors light that passes through the sensors on the end of the optical fiber 150 instead of light that reflects off of the sensors. In operation, the optics 174 direct light that passes through the sensors to the detector 166. The rest of the operation is essentially the same as described above with reference to FIG. 12.

Another alternative embodiment of a spectral multiplexing system 183 for use with a transmissive-type sensor is depicted in FIG. 13. In the spectral multiplexing system of FIG. 13, the surface sensing system 154 is illuminated externally (e.g., the illuminating light is not initially injected into the optical fiber 150 that includes the surface sensing system 154). Light from the light source that passes through the surface sensing system and propagates up fiber 150 is detected by the OSA 156. In another embodiment, the OSA is a detector and the light source is a tunable laser source as described above with reference to FIGS. 10 and 12.

Although some examples of spectral multiplexing systems 142, 162, 172, 182, and 183 are described with reference to FIGS. 9–13, other configurations are possible. For example, spectral multiplexing in a single fiber can be applied to multiple fibers that are bundled together to increase the number or detection channels that are available. In another alternative configuration, the light source is a set of narrowband light sources, with the sources being activated in sequence to cover the desired wavelength range.

FIG. 14 depicts a process flow diagram of a method for characterizing one or more physical properties of a test medium in accordance with the invention. At block 300, first and second sensors are exposed to a test medium, wherein the first and second sensors are configured such that the first and second sensors exhibit resonant frequencies or Q-factors that are distinguishable from each other. At block 302, an optical signal is injected into the optical fiber such that the optical signal interacts with the first and second sensors in parallel. At block 304, the optical signal is detected after it has interacted with the first and second sensors.

Implementing spectral multiplexing with a surface sensing system that has sensors with different resonant frequencies and/or Q-factor located on the end of the same optical fiber enables different physical properties of a test medium to be characterized in parallel. Physical properties of the test medium that can be characterized include, but are not limited to, temperature, pressure, biological makeup, and chemical makeup. As described above, different physical properties can be characterized in parallel. For example, the temperature of a test medium and the concentration of a particular protein in the test medium can be characterized in parallel using two different sensors located on the end of the same optical fiber.

An advantage of the spectral multiplexing systems 142, 162, 172, 182, and 183 described with reference to FIGS. 9–13 is that spectral multiplexing is accomplished with a single optical signal source 144, 164 and a single detector 156, 166.

Surface sensors have been used to enhance the collection efficiency of fluorescence. In particular, metal structures (e.g., periodic or uniform) have been used to engineer radiative decay time of fluorophores as well as direct the normally isotropic emission from fluorophores into specific angles. This technique is described in "Radiative decay engineering 5: metal-enhanced fluorescence and plasmon emission," Joseph R. Lakowicz, Analytical Biochemistry, vol. 337, Issue 2, 15 Feb. 2005, pages 171–194, which is incorporated by reference herein. In an embodiment in accordance with the invention, at least two different sensors located at the end of the same fiber are configured to couple fluorescence from a fluorophore or fluorophores with increased efficiency. In particular, the sensors at the end of the same fiber are configured to be wavelength-dependent such that the collection efficiency of at least two different colors of fluorescence is enhanced. Enhancing the collection efficiency of two different colors of fluorescence using at least two sensors located at the end of the same fiber enables spectral multiplexing. The sensors on the end of the same fiber also act to localize the electromagnetic fields, thereby reducing the background fluorescence noise.

Although grating-based sensors are described as one exemplary type of sensor, other sensor structures can be located on the end of the same fiber to enable spectral multiplexing in a surface sensing system.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A sensor comprising:
   an optical fiber having an end;
   a first sensor located on the end of the optical fiber; and
   a second sensor located on the end of the optical fiber;
   wherein the first and second sensors are configured such that the first and second sensors exhibit resonant frequencies or Q-factors that are distinguishable from each other.

2. The sensor of claim 1 wherein the first sensor has a spatial profile of regions of high and low dielectric constant that results in a first resonant frequency and Q-factor and wherein the second sensor has a spatial profile of regions of high and low dielectric constant that results in a second resonant frequency and Q-factor.

3. The sensor of claim 2 wherein the spatial profiles of the first and second sensors include patterns of low dielectric constant features.

4. The sensor of claim 3 wherein the low dielectric constant features of the two sensors are at a different pitch.

5. The sensor of claim 2 wherein an aspect of the spatial profile of the first sensor is different from the same aspect of the spatial profile of the second sensor.

6. The sensor of claim 1 wherein the first and second sensors cover non-overlapping portions of the optical fiber end.

7. The sensor of claim 1 further comprising a spectral multiplexing system in optical communication with the optical fiber configured to enable parallel detection of an optical signal that interacts with the first and second sensors.

8. The sensor of claim 7 wherein the spectral multiplexing system includes a tunable laser source wherein the wavelength range of the tunable laser source includes the resonant frequencies of the first and second sensors.

9. The sensor of claim 1 further comprising a spectral multiplexing system in optical communication with the optical fiber, the spectral multiplexing system having an optical signal source configured to provide a swept optical signal to the optical fiber and a detector configured to detect portions of the optical signal that interact with the first and second sensors.

10. The sensor of claim 1 wherein the first and second sensors are fabricated on the end of the optical fiber.

11. A method for characterizing one or more physical properties of a test medium, the method comprising:
   exposing first and second sensors to a test medium, wherein the first and second sensors are located on the end of the same optical fiber and configured such that the first and second sensors exhibit resonant frequencies or Q-factors that are distinguishable from each other;
   injecting an optical signal into the optical fiber such that the optical signal interacts with the first and second sensors in parallel; and
   detecting the optical signal after it has interacted with the first and second sensors.

12. The method of claim 11 wherein the optical signal has a broadband optical energy spectrum that includes the resonant frequencies of the first and second sensors.

13. The method of claim 11 wherein the optical signal has a narrowband optical energy spectrum, the method further comprising sweeping the optical signal across a range of wavelengths that includes the resonant frequencies of the first and second sensors.

14. The method of claim 13 wherein the detecting comprises detecting the optical signal with a single optical detector.

15. The method of claim 11 further including monitoring shifts in the resonant frequencies associated with the first and second sensors.

16. The method of claim 11 wherein the detecting comprises detecting the optical signal with a single optical detector.

17. A sensor system comprising:
   an optical fiber having an end;
   a first sensor located on the end of the optical fiber;

a second sensor located on the end of the optical fiber, wherein the first and second sensors are configured such that the first and second sensors exhibit a distinguishable difference in at least one of resonant frequency and Q-factor; and a spectral multiplexing system in optical communication with the optical fiber, the spectral multiplexing system having an optical signal source configured to provide an optical signal to the optical fiber and a detector configured to detect portions of the optical signal that interact with the first and second sensors.

18. The sensor system of claim 17 wherein the first and second sensors have spatial profiles of regions of high and low dielectric constant that include patterns of low dielectric constant features.

19. The sensor system of claim 18 wherein the low dielectric constant features of the two sensors are at a different pitch.

20. The sensor system of claim 19 wherein the first and second sensors cover non-overlapping portions of the optical fiber end.

* * * * *